United States Patent [19]

Krassó et al.

[11] Patent Number: 4,599,347
[45] Date of Patent: Jul. 8, 1986

[54] TETRAHYDRO-NAPHTH (2,3-D) IMIDAZOLE DERIVATIVES

[75] Inventors: Anna Krassó, Basel; Henri Ramuz, Birsfelden, both of Switzerland

[73] Assignee: Hoffmann-La Roche Inc., Nutley, N.J.

[21] Appl. No.: 560,699

[22] Filed: Dec. 12, 1983

Related U.S. Application Data

[62] Division of Ser. No. 290,032, Aug. 5, 1981, Pat. No. 4,435,406.

[30] Foreign Application Priority Data

Aug. 21, 1980 [CH] Switzerland ............... 6321/80

[51] Int. Cl.[4] ............... A61K 31/44; C07D 401/12
[52] U.S. Cl. ............... 514/338; 546/271
[58] Field of Search ............... 546/271; 424/263; 514/338

[56] References Cited

U.S. PATENT DOCUMENTS 4,182,766 1/1980 Krasso et al. ............... 546/271

FOREIGN PATENT DOCUMENTS 0005129 10/1979 European Pat. Off. .

OTHER PUBLICATIONS

G. Sundell et al. Acta Physicol. Scand. Suppl. 473,41 (1979).

Primary Examiner—Jane T. Fan
Attorney, Agent, or Firm—Jon S. Saxe; Bernard S. Leon; Matthew Boxer

[57] ABSTRACT

Tricyclic imidazole derivatives of the formula

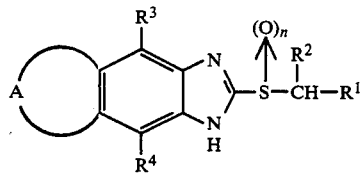

wherein $R^1$ is 2-pyridyl optionally substituted by lower alkyl or lower alkoxy, n is the integer 0 to 1, $R^2$ is hydrogen or lower alkyl, $R^3$ and $R^4$, independently, are hydrogen or lower alkyl, A is a group of the formula

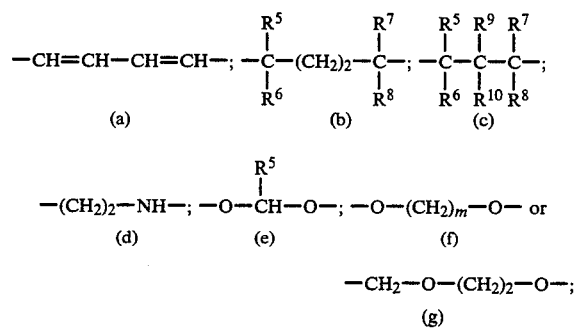

m is the integer 2 or 3, $R^5$, $R^6$, $R^7$ and $R^8$, independently, are hydrogen or lower alkyl, and $R^9$ is hydrogen and $R^{10}$ is hydrogen or lower alkyl or $R^9$ and $R^{10}$ taken together are oxo, provided that at least one of $R^3$ and $R^4$ is lower alkyl when A is a group of the formula —CH=CH—CH=CH— or —(CH$_2$)$_4$—, and their pharmaceutically acceptable acid addition salts. The compounds of formula I inhibit gastric acid secretion and prevent the formation of gastric ulcers.

16 Claims, No Drawings

TETRAHYDRO-NAPHTH (2.3-D) IMIDAZOLE DERIVATIVES

This is a division of application Ser. No. 290,032, filed Aug. 5, 1981 now U.S. Pat. No. 4,435,406 issued Mar. 8, 1984.

BRIEF SUMMARY OF THE INVENTION

The invention relates to tricyclic imidazole derivatives of the formula

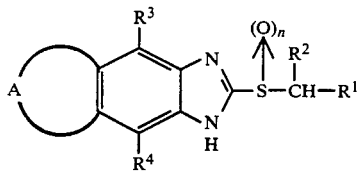

wherein $R^1$ is 2-pyridyl optionally substituted by lower alkyl or lower alkoxy, n is the integer 0 or 1, $R^2$ is hydrogen or lower alkyl, $R^3$ and $R^4$, independently, are hydrogen or lower alkyl, A is a group of the formula

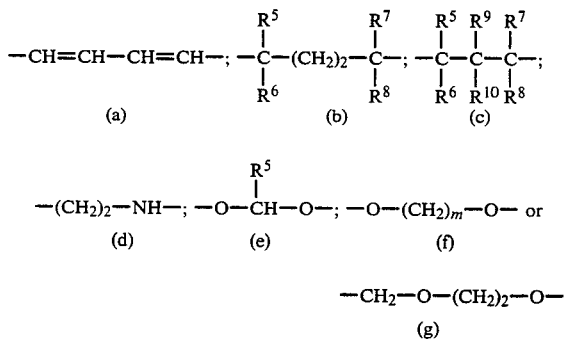

m is the integer 2 or 3, $R^5$, $R^6$, $R^7$ and $R^8$, independently, are hydrogen or lower alkyl, and $R^9$ is hydrogen and $R^{10}$ is hydrogen or lower alkyl or $R^9$ and $R^{10}$ taken together are oxo, provided that at least one of $R^3$ and $R^4$ is lower alkyl when A is a group of the formula $$-CH=CH-CH=CH- \text{ or } (CH_2)_4-,$$

and their pharmaceutically acceptable acid addition salts. The compounds of formula I inhibit gastric acid secretion and prevent the formation of ulcers. In another aspect the invention relates to pharmaceutical compositions comprising the compounds of formula I.

In yet another aspect the invention relates to the use of the compounds of formula I to inhibit gastric acid secretion and the prevention of gastric ulcers.

DETAILED DESCRIPTION OF THE INVENTION

The invention is concerned with imidazole derivatives, namely, tricyclic imidazole derivatives of the formula

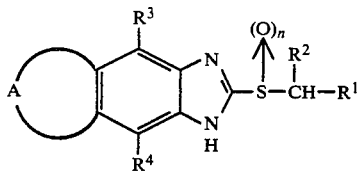

wherein $R^1$ is 2-pyridyl optionally substituted by lower alkyl or lower alkoxy, n is the integer 0 or 1, $R^2$ is hydrogen or lower alkyl, $R^3$ and $R^4$, independently, are hydrogen or lower alkyl, A is a group of the formula

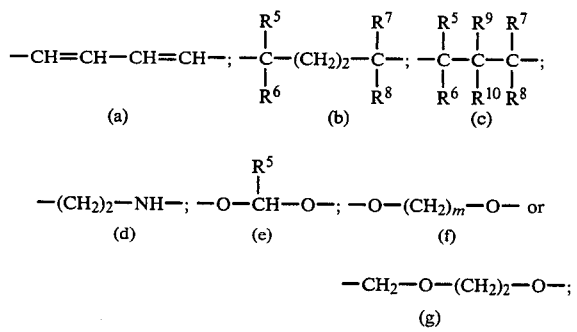

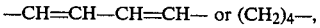

m is the integer 2 or 3, $R^5$, $R^6$, $R^7$ and $R^8$, independently, are hydrogen or lower alkyl, and $R^9$ is hydrogen and $R^{10}$ is hydrogen or lower alkyl or $R^9$ and $R^{10}$ taken together are oxo, provided that at least one of $R^3$ and $R^4$ is lower alkyl when A is a group of the formula $$-CH=CH-CH=CH- \text{ or } (CH_2)_4-,$$

and their pharmaceutically acceptable acid addition salts.

The compounds of formula I are distinguished by valuable pharmacodynamic properties. Specifically, they inhibit gastric acid secretion and the formation of ulcers. Objects of the invention are the compounds of formula I and their pharmaceutically acceptable acid addition salts, the preparation of the compounds of formula I and their salts, medicaments containing a compound of formula I or a salt thereof and the preparation of such medicaments, as well as the use of the compounds of formula I and their salts in the control or prevention of illnesses, especially, in the inhibition of gastric acid secretion and/or in the prevention of ulcers.

As used herein, the term "lower alkyl" denotes straight-chain and branched alkyl groups containing 1-7 carbon atoms, preferably up to 4 carbon atoms such as methyl, ethyl, n-propyl, isopropyl, n-butyl, isobutyl and the like. The term "lower alkoxy" denotes lower alkyl ether groups in which "lower alkyl" has the above significance.

A preferred group of compounds of formula I comprises those in which A is a group of formula (c) described above, wherein $R^5$, $R^6$, $R^7$ and $R^8$ all have the same significance, namely, hydrogen or lower alkyl, $R^3$ and $R^4$ are each hydrogen and $R^9$ and $R^{10}$ are as described above, that is, a compound of the formula

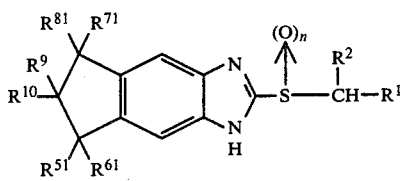

wherein $R^1$, $R^2$, $R^9$, $R^{10}$ and n are as previously described in formula I and $R^{51}$, $R^{61}$, $R^{71}$ and $R^{81}$ all have the same significance, namely, hydrogen or lower alkyl.

Especially preferred compounds of formula Ia are those wherein $R^{51}$, $R^{61}$, $R^{71}$ and $R^{81}$ all are hydrogen or all are methyl.

A further preferred group of compounds of formula I comprises those in which A is a group of formula (e), (f) or (g) set forth above.

Furthermore, generally, $R^2$ is preferably hydrogen and $R^1$ is preferably 2-pyridyl or 2-pyridyl monosubstituted by lower alkyl, especially methyl, preferably 5-methyl-2-pyridyl.

Especially preferred compounds of formula I are:
5,7-Dihydro-5,5,7,7-tetramethyl-2-[(2-pyridylmethyl)-thio]indeno(5,6-d)imidazol-6-(1H)-one,
6-[(2-pyridylmethyl)thio]-5H-1,3-dioxolo(4,5-f)benzimidazole,
6-[[(5-methyl-2-pyridyl)methyl]thio]-5H-1,3-dioxolo(4,5-f)benzimidazole,
6-[[5-methyl-2-pyridyl)methyl]sulfinyl]-5H-1,3-dioxolo(4,5-f)benzimidazole and
1,5,6,7-tetrahydro-2-[[(5-methyl-2-pyridyl)methyl]thio]indeno(5,6-d)imidazole.

Other representative examples of compounds of formula I are:
4-Methyl-2-[[(5-methyl-2-pyridyl)methyl]thio]-1H-naphth(2,3-d)imidazole,
4-methyl-2-[(2-pyridylmethyl)thio]-1H-naphth(2,3-d)imidazole,
4-methyl-2-[[1-(2-pyridyl)ethyl]thio]-1H-naphth(2,3-d)imidazole,
5,6,7,8-tetrahydro-5,5,8,8-tetramethyl-2-[(2-pyridylmethyl)thio]-1H-naphth(2,3-d)imidazole,
5,6,7,8-tetrahydro-5,5,8,8-tetramethyl-2-[[(5-methyl-2-pyridyl)methyl]thio]-1H-naphth(2,3-d)imidazole,
5,7-dihydro-5,5,7,7-tetramethyl-2-[[(5-methyl-2-pyridyl)methyl]thio]indeno(5,6-d)imidazol-6(1H)-one,
5,7-dihydro-5,5,7,7-tetramethyl-2-[(2-pyridylmethyl)-sulfinyl]indeno(5,6-d)imidazol-6-(1H)-one,
2-methyl-6-[[(5-methyl-2-pyridyl)methyl]thio]-5H-1,3-dioxolo(4,5-f)benzimidazole,
2-methyl-6-[(2-pyridylmethyl)thio]-5H-1,3-dioxolo-(4,5-f)benzimidazole,
2,2-dimethyl-6-[(2-pyridylmethyl)thio]-5H-1,3-dioxolo(4,5-f)benzimidazole,
2,2-dimethyl-6-[[(5-methyl-2-pyridyl)methyl]thio]-5H-1,3-dioxolo(4,5-f)benzimidazole,
1,5,6,7-tetrahydro-2-[(2-pyridylmethyl)thio]pyrrolo-2,3-f)benzimidazole,
1,5,6,7-tetrahydro-2-[[(5-methyl-2-pyridyl)methyl]thio]pyrrolo(2,3-f)benzimidazole,
1,5,6,7-tetrahydro-2-[[(5-methyl-2-pyridyl)methyl]-sulfinyl]indeno(5,6-d)imidazole,
1,5,6,7-tetrahydro-2-[(2-pyridylmethyl)sulfinyl-indeno(5,6-d)imidazole,
6,7-dihydro-2-[(2-pyridylmethyl)thio]-1H-p-dioxino-(2,3-f)benzimidazole,
6,7-dihydro-2-[[(5-methyl-2-pyridyl)methyl]thio]-1H-p-dioxino(2,3-f)benzimidazole,
1,8-dihydro-2-[[(5-methyl-2-pyridyl)methyl]thio]-m-dioxino(4,5-f)benzimidazole,
1,8-dihydro-2-[(2-pyridylmethyl)thio]-m-dioxino-(4,5-f)benzimidazole,
7,8-dihydro-2-[(2-pyridylmethyl)thio]-1H,6H,(1,4)-dioxepino(2,3-f)benzimidazole and
7,8-dihydro-2-[[(5-methyl-2-pyridyl)methyl]thio]-1H,6H-(1,4)dioxepino(2,3-f)benzimidazole.

The compounds of formula I and their salts can be prepared in accordance with the invention as follows:

(a) for the preparation of compounds of formula I in which n is the integer 0, reacting a compound of the formula

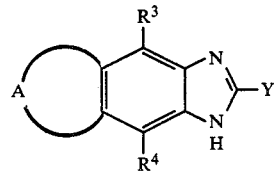

wherein $R^3$, $R^4$ and A are as previously described and Y is as hereinafter described,
with a compound of the formula

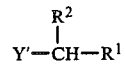

wherein $R^1$ and $R^2$ are as previously described and Y' is as hereinafter described,
wherein one of Y and Y' is a mercapto group and the other is a leaving group, or (b) for the preparation of compounds of formula I in which n is the integer 1, oxidizing a corresponding compound of formula I in which n is the integer 0, if desired, separating a diastereoisomeric mixture which may be obtained into the diastereoisomeric racemates and/or resolving a racemate which may be obtained into the two antipodes and/or converting a free base obtained into a pharmaceutically acceptable acid addition salt and/or converting an acid addition salt obtained into the free base or into another acid addition salt.

According to a first process aspect in accordance with the invention, a compound of formula II is reacted with a compound of formula III, wherein either the symbol Y in formula II is a mercapto group and the symbol Y' in formula III is a leaving group or the symbol Y in formula II is a leaving group and the symbol Y' in formula III is a mercapto group. Leaving groups are, for example, halogen, especially chlorine, bromine or iodine, or acid groups, for example, the residue of a strong organic sulfonic acid, for example, an arylsulfonyloxy group such as tosyloxy, or an alkylsulfonyloxy group such as mesyloxy. Other examples of leaving groups are alkylmercapto groups such as methylmercapto, or alkylsulfinyl groups such as methylsulfinyl. The reaction of a compound of formula II with a compound of formula III is conveniently carried out in the presence of a solvent or solvent mixture which is inert under the reaction conditions and, if desired, in the presence of a base. Suitable bases for this purpose are especially inorganic bases such as sodium or potassium hydroxide, sodium or potassium hydride and the like or organic bases such as triethylamine or other tertiary amines. The reaction of a compound of formula II with a compound of formula III can also be carried out in a two-phase system under catalysis.

Especially suitable as the solvent or solvent mixture are alcohols such as ethanol, mixtures of alcohols and water, ethers such as tetrahydrofuran, halogenated hydrocarbons such as methylene chloride or chloroform. Dimethylformamide is a preferred solvent.

The reaction temperature is variable in fairly wide limits; it usually lies between room temperature and the boiling point of the reaction mixture. The reaction is preferably carried out at the boiling point of the reaction mixture. A convenient embodiment of the present process aspect comprises first converting a compound of formula II in which Y' is the acid group of a reactive ester. In a preferred embodiment, the reaction is carried out in dimethylformamide in the presence of a base while warming.

In another process aspect in accordance with the invention, a compound of formula I in which n is the integer 0, is oxidized. A sulfur atom is thereby converted into the sulfinyl group. Oxidizing agents which are customary for such conversions are utilized; for example, peracids such as m-chloro-perbenzoic acid, hydrogen peroxide, peresters, sodium metaperiodate, selenium dioxide, manganese dioxide and the like. The oxidation is conveniently carried out in an organic solvent which is inert under the reaction conditions; for example, in a halogenated hydrocarbon such as methylene chloride, chloroform, dichloroethane and the like or in a hydrocarbon such as benzene and the like. When hydrogen peroxide is used as the oxidizing agent, the oxidation can also be carried out in aqueous acetic acid, acetic acid and the like. It is advantageous to use the oxidizing agent in slight excess with reference to the compound to be oxidized. The oxidation is conveniently carried out at room temperature or below room temperature.

Depending on the structure of the starting material and/or on the aspect of the process of the invention which is used, certain compounds of formula I can exist as optical isomers or as racemates or, when they contain at least two asymmetric centers, as diastereoisomeric mixtures or racemate mixtures. Diastereoisomeric mixtures and racemate mixtures obtained can be separated on the basis of physical-chemical differences of the components; racemates can be resolved according to known methods; for example, by fractional crystallization of salts formed with optically active acids.

Depending on the process conditions and the starting materials used, the compounds of formula I are obtained either as free bases or as acid addition salts. The free bases can be converted into corresponding acid addition salts by reaction with organic or inorganic acids. Preferably acids which form therapeutically compatible or pharmaceutically acceptable salts are used, for example, hydrochloric acid, hydrobromic acid, phosphoric acid, sulfuric acid, citric acid, acetic acid, succinic acid, maleic acid, p-toluene-sulfonic acid and the like. The acid addition salts of the compounds of formula I can be converted in a known manner into the corresponding free bases or into other acid addition salts.

Representative compounds of formula I of the invention were tested for their gastric acid secretion-inhibiting activity, for their anti-ulcer activity, as well as for their toxicity.

The two experimental procedures described hereinafter were used to determine the gastric acid secretion-inhibiting activity:

Shay test

The pylorus of female rats, which had received no food for 24 hours but which had received water ad libitum, is ligatured under slight ether narcosis in accordance with Shay et al. [Gastroenterology 5, 43 (1945)]. Immediately thereafter the substances to be tested are administered intraduodenally to the animals. Four (4) hours later the animals are killed. The volume and the acidity of their gastric juice are determined and the values obtained are compared with those of control animals which were treated similarly, but had received no test substance. The ED 50 is defined as the dosage of test substance which brings about a 50% reduction of volume or acidity of the gastric juice in the treated animals compared with the control animals.

Heidenhain test

A part of the stomach fundus of female and male dogs is separated from the remaining stomach in the form of a pouch according to the Hidenhain technique [described by Rudick et al. in J. Surgical Research 7, 383–398 (1967)]. In the pouch there is fitted a steel cannula which is conducted externally through the abdominal wall. The secretion experiments are commenced after about 6 weeks. Before each experiment the animals receive no food for 18 hours, but receive water ad libitum. They are conscious during the experiment. A saphenous vein is cannulated for an infusion of 4-methylhistamine dihydrochloride, a selective stimulator of the histamine $H_2$-receptors. An appropriate infusion rate of the 4-methylhistamine dihydrochloride (20, 40 or 80 g/kg per hour, intravenously) is ascertained for each animal in preliminary experiments. During the entire main experiment the gastric secretion is stimulated by the infusion of 4-methylhistamine dihydrochloride, and 15 minute fractions of the gastric juice are collected continuously. As soon as volume and pH of these fractions show constant values, the test substances are administered orally. The ED 50 is defined as that dosage of test substance which brings about a 50% inhibition of the acid secretion caused by 4-methylhistamine dihydrochloride in the treated animals compared with the controls.

The anti-ulcer activity of the compounds of formula I of the invention was demonstrated by the following experiment:

The combined repeated administration of small doses of 4-methylhistamine and carbachol leads to the regular appearance of ulcers of the duodenum and only to little or no superficial damage of the stomach.

Before the beginning of the testing a group of 10 guinea pigs, body weight 280 to 320 g, of the same sex receives no food for 24 hours, but receives water ad libitum. Various doses of the test substance or of the appropriate vehicle (control) are administered intragastrically.

The test is repeated on different days with other groups of guinea pigs in order to avoid the influence of daily variations.

In Table I, which follows, the names of the compounds tested as well as the results of the testing for their gastric secretion-inhibiting activity, for their anti-ulcer activity and for their toxicity are given.

TABLE 1

| Compound | Prel. tox mouse mg/kg p.o. | Shay test ED 50 (mg/ kg i.d.) | | Heidenhain test (mg/kg p.o.)/ ED 50 | Anti-ulcer ED 50 (mg/kg i.g.) |
| --- | --- | --- | --- | --- | --- |
| | | Vol | Acid | | |
| 5,7-Dihydro-5,5,7,7-tetra-methyl-2-[(2-pyridylmethyl)-thio]indeno(5,6-d)imidazole-6(1H)—one | 2500 | 20 | 9 | 5.5 | 32 |
| 6-[(2-Pyridylmethyl)thio]-5H—1,3-dioxolo(4,5-f)-benzimidazole. 2HCl | 1250 | 35 | 29 | 2.6 | 17 |
| 6-[[(5-Methyl-2-pyridyl)-methyl]thio]-5H—1,3-dioxolo-(4,5-f)benzimidazole | 5000 | 100 | 100 | 1.8 | 18 |
| 6-[[(5-Methyl-2-pyridyl)-methyl]thio]-5H—1,3-dioxolo-(4,5-f)benzimidazole dihydrochloride | 625 | 75 | 65 | 2.1 | 25 |
| 1,5,6,7-Tetrahydro-2-[[(5-methyl-2-pyridyl)methyl]-thio]indeno(5,6-d)imidazole 2HCl | 1250 | 50 | 28 | 3.6 | 34 |
| 6-[[(5-Methyl-2-pyridyl)-methyl]sulphinyl]-5H—1,3-dioxolo(4,5-f)benzimidazole | 5000 | 65 | 28 | 2.3 | 14 |

The compounds of formula I and the pharmaceutically acceptable acid addition salts thereof can therefore be used as medicaments, for example, in the form of pharmaceutical preparations. The pharmaceutical preparations can be administered orally, for example in the form of tablets, coated tablets, dragees, hard and soft gelatin capsules, solutions, emulsions or suspensions. The administration can, however, also be carried out rectally, for example, in the form of suppositories, or parenterally, for example, in the form of injection solutions.

As mentioned earlier, medicaments containing a compound of formula I or a pharmaceutically acceptable acid addition salt thereof also form part of the invention, as well as the process for the preparation of such medicaments which comprises bringing one or more compounds of formula I or pharmaceutically acceptable acid addition salts thereof and, if desired, one or more other therapeutically valuable substances into a galenical administration form.

For the preparation of tablets, coated tablets, dragees and hard gelatin capsules, the compounds of formula I or pharmaceutically acceptable acid addition salts thereof can be processed with pharmaceutically inert, inorganic or organic excipients. Examples of excipients which can be used, for example, for tablets, dragees and hard gelatin capsules are lactose, maize starch or derivatives thereof, talc, stearic acid or its salts and the like.

Suitable excipients for soft gelatin capsules are, for example, vegetable oils, waxes, fats, semi-solid and liquid polyols and the like.

Suitable excipients for the preparation of solutions and syrups are, for example, water, polyols, saccharose, invert sugar, glucose and the like.

Suitable excipients for injection solutions are, for example, water, alcohols, polyols, glycerine, vegetable oils and the like.

Suitable excipients for suppositories are, for example, natural or hardened oils, waxes, fats, semi-liquid or liquid polyols and the like.

Moreover, the pharmaceutical preparations can contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances.

In accordance with the invention, the compounds of formula I and the pharmaceutically acceptable acid addition salts thereof can be used in the control or prevention of illnesses, for example, in the inhibition of the gastric acid secretion and/or in the prevention of ulcers. The dosage for such uses can vary within wide limits and is, of course, adjusted to the individual requirements in each particular case. In general, in the case of oral administration a daily dosage of about 100–400 mg can be used and in the case of intravenous administration a daily dosage of about 5–20 mg can be used.

The starting materials of formulas II and III belong to classes of compounds which are known. Individual compounds which have not yet been described, can be prepared without difficulties in analogy to the methods of preparing the known compounds.

The Examples which follow further illustrate the invention. In these examples all temperatures are given in degrees centigrade unless otherwise stated.

EXAMPLE 1

Preparation of 4-methyl-2-[[(5-methyl-2-pyridyl)methyl]thio]-1H-naphth(2,3,d)imidazole dihydrochloride 10.2 g of 4-methyl-1H-naphth(2,3-d)-imidazole-2-thiol were suspended in 150 ml of alcohol in a 500 ml sulfonation flask equipped with stirrer, thermometer, dropping funnel and condenser. To the above was added dropwise a solution of 5.4 g of NaOH in 75 ml of water and the solution was stirred at room temperature for 30 minutes. After adding 14.6 g of 2-chloromethyl-5-methylpyridine hydrochloride, the mixture was boiled at reflux overnight and subsequently evaporated. The residue, dissolved in ethyl acetate, was extracted with 3N sodium hydroxide, washed neutral with water, dried over sodium sulfate and evaporated in vacuo. The crude product was dissolved in methylene chloride, the solution was filtered and the filtrate was evaporated. 16.2 g of oil were placed on a column prepared from 200 g of silicon dioxide in toluene and the column was eluted with toluene/ethyl acetate (1:1). The fractions which contained the main amount were evaporated together, dissolved in 40 ml of alcohol and treated with 100 ml of tN hydrochloric acid in ethyl acetate. There were obtained 10.2 g (54.5% of theory) of 4-methyl-2-[[(5-methyl-2-pyridyl)methyl]thio]-1H-naphth(2,3,-d)imidazole dihydrochloride of melting point 233°–235° C.

4-Methyl-2[(2-pyridyl)methyl)thio]-1H-naphth(2,3-d)-imidazole dihydrochloride of melting point 223°–225° C. and 4-methyl-2-[[1-(2-pyridyl)ethyl]thio]-1H-naphth-(2,3-d)imidazole dihydrochloride of melting point 208°–209° C. were prepared analogously.

Preparation of the starting material 120 g of 2,3-dihydroxynaphthalene, 132 g of ZN(CN)$_2$(zinc cyanide) and 1.32 g of potassium chloride in 1200 ml of absolute ether were placed in a 2.5 l sulfonation flask equipped with inlet-tube, stirrer, thermometer, reflux condenser and calcium chloride tube. Hydrogen chloride gas was introduced for 6 hours while cooling with ice and stirring. Subsequently, the ether was decanted and destroyed with sodium hydroxide. In order to remove the residual ether, the oily residue was evacuated hot, then treated with 800 ml of water and stirred at 60° C. on a steam-bath. The cooled mixture was filtered under suction and the material on the suction filter was dried at 40 ° C. in vacuo. The crude product was dissolved in acetonitrile while warming, filtered and, after concentration in vacuo, crystallized. There were obtained 121.3 g (85.7% of theory) of 2,3-dihydroxy-naphthaldehyde of melting point 132°–133° C.

86.0 g of semicarbazide hydrochloride dissolved in 500 ml of water and 103 g of sodium acetate (CH$_3$COONa.3H$_2$O) were placed in a 2.5 l sulfonation flask equipped with stirrer, thermometer and dropping funnel. At an internal temperature of 40°–50° C., there was added dropwise a solution of 138.4 g of 2,3-dihydroxy-naphthaldehyde in 1000 ml of methanol. The mixture was stirred at 40°–50° C. for 1 hour and then, after adding 2 l of water, cooled to 10° C. and suction filtered. The material on the suction filter was back-washed thoroughly with water and dried at 60° C. in vacuo. Recrystallization from glacial acetic acid gave 131.9 g (73.1% of theory) of 2,3-dihydroxy-naphthaldehyde semicarbazone of melting point 210°–215° C.

131 g of 2,3-dihydroxy-naphthaldehyde semicarbazone were boiled at reflux overnight with 250 g of powdered potassium hydroxide in 1350 ml of diethylenegly-col under an argon stream in a 1.5 l sulfonation flask equipped with stirrer, condenser, theremometer and calcium chloride tube. The cooled solution was diluted with 4,5 l of water, made acid with 450 ml of concentrated hydrochloric acid and extracted eight times with 1 l ether. The combined ether extracts were dried over sodium sulfate and evaporated in vacuo. Recrystallization from water gave 61.5 (65.5% of theory) of 1-methyl-2,3-dihydroxy-naphthalene. Melting point 97°–100° C.

30.1 of 1-methyl-2,3-dihydroxy-naphthalene in 1000 ml of 25% ammonia were shaken in a 5 l autoclave at 240° C. and 30 bar of nitrogen for 60 hours. The prouct was removed by filtration under suction, back-washed with a small amount of water and dissolved in 3 l of ethyl acetate. The solution was extracted twice with 500 ml of 3N sodium hydroxide, washed neutral with water, dried over sodium sulfate and evaporated in vacuo. The residue, 10.2 g (34.3% of theory) of an oil, 1-methyl-1,2-diaminonaphthalene, were dissolved in a small amount of ethyl acetate and acidified with 5N hydrochloric acid in ethyl acetate. Recrystallization from methanol/ether gave 11.2 g (26.5% of theory) of 1-methyl-2,3-diamino-naphthalene dihydrochloride with a melting point of 288°–289° C.

16.9 g of 1-methyl-2,3-diamino-naphthalene (crude base) were suspended in 250 ml of alcohol in a 500 ml sulfonation flask equipped with stirrer, thermometer and reflux condenser and, after adding 25 ml of water as well as 18.8 g of potassium ethylxanthate, recrystallized from isopropanol, boiled at reflux overnight. The insoluble particles were removed by filtration, the solution was diluted with 200 ml of water and made neutral with 10–15 ml of glacial acetic acid. After stirring at 60°–70° C. for 1 hour, the mixture was cooled and suction filtered. There were obtained 10.2 g (48.5% of theory) of 4-methyl-1H-naphth(2,3-d)imidazole-2-thio with a melting point above 300° C.

EXAMPLE 2

Preparation of 5,6,7,8-tetrahydro-5,5,8,8-tetramethyl-2-[(2-pyridylmethyl)thio]-1H-naphth(2,3-d)imidazole 9.0 g of 5,6,7,8-tetrahydro-5,5,8,8-tetramethyl-1H-naphth(2,3-d)imidazole-2-thiol were suspended in 60 ml of alcohol in a 250 ml sulfonation flask equipped with stirrer, thermometer, dropping funnel and reflux condenser. A solution of 3.24 g of sodium hydroxide in 20 ml of water was added dropwise thereto while stirring well and the mixture was stirred at room temperature for an additional 30 minutes. After adding 6.0 g of 2-chloromethyl-pyridine hydrochloride, the mixture was boiled at reflux overnight and subsequently evaporated. The residue was taken up in 1 l of ethyl acetate, washed neutral three times with 250 ml of water, dried over sodium sulfate and, after evaporation in vacuo, recrystallized from acetonitrile. There were obtained 7.0 g (57.3% of theory) of 5,6,7,8-tetrahydro-5,5,8,8-tetramethyl-2-[(2-pyridylmethyl)thio]-1H-naphth(2,3-d)-imidazole of melting point 199°–200° C.

5,6,7,8-Tetrahydro-5,5,8,8-tetramethyl-2-[[(5-methyl-2-pyridyl)methyl]thio]-1H-naphth(2,3-d)imidazole of melting point 187°–188° C. was prepared analogously.

Preparation of the starting material 18.8 g of 5,6,7,8-tetrahydro-5,5,8,8-tetramethyl-naphthalene were dissolved in 75 ml of concentrated sulfuric acid in a 500 ml sulfonation flask equipped with stirrer, thermometer, dropping funnel and calcium chloride tube and nitrated by the dropwise addition of 75 ml of fuming nitric acid (3=1.5) at 0°–5° C. (methanol/ice bath). After the dropwise addition of the nitric acid, the mixture was stirred at room temperature for 3 hours, then poured onto ice and extracted twice with 1 l of methylene chloride. The organic phase was washed twice with 500 ml of water, dried over sodium sulfate and evaporated in vacuo. The crude product, 22.2 g of red-brown crystals of melting point 203°–204° C., was filtered through 450 g of silicon dioxide with toluene/n-heptane (1:1). There were obtained 11.0 g (47.3% of theory) of 5,6,7,8-tetrahydro-5,5,8,8-tetramethyl-2,3-dinitro-naphthalene, in the form of light yellow crystals crystallized from cyclohexane, of melting point 203°–204° C.

39.0 g of 5,6,7,8-tetrahydro-5,5,8,8-tetramethyl-2,3-dinitro-naphthalene in 1300 ml of methanol were hydrogenated with Raney-nickel in a 2 l hydrogenation flask. The $H_2$-uptake after 48 hours was 20.7 l (18.8 l=theory). The catalyst was removed by filtration under suction, the solution was again filtered and the filtrate was evaporated in vacuo. The residue was crystallized from isopropanol. There were obtained 26.2 g (85.5% of theory) of 5,6,7,8-tetrahydro-5,5,8,8-tetramethyl-2,3-naphthalene-diamine of melting point 188°–189° C.

21.8 g of 5,6,7,8-tetrahydro-5,5,8,8-tetramethyl-2,3-naphthalenediamine were suspended in 120 ml of alcohol in a 250 ml sulfonation flask equipped with stirrer, thermometer, dropping funnel and reflux condenser. There were added dropwise thereto firstly a solution of 6.3 g of potassium hydroxide in 20 ml of water and, after stirring at room temperature for 1 hour, 8.9 g (d=1.2705) of carbon disulfide. After an additional hour, the solution was stirred and then boiled at reflux overnight. After adding 11.3 g of potassium hydroxide in 45 ml of water, the mixture was stirred for an additional 1 hour. The hot solution was then filtered through a carbon filter and the filtrate was diluted with 120 ml of water. To this was added dropwise at 60°–70° C. 60 ml of 50% acetic acid and the mixture was stirred at this temperature for an additional 1 hour. The cold suspension was suction filtered and the material on the suction filter was recrystallized from isopropanol. There were obtained 22.7 g (87.5% of theory) of 5,6,7,8-tetrahydro-5,5,8,8-tetramethyl-1H-naphth(2,3-d)imidazole-2-thiol of melting point above 300° C.

EXAMPLE 3

Preparation of 5,7-dihydro-5,5,7,7-tetramethyl-2-[(2-pyridylmethyl)-thio]indeno(5,6-d)imidazole-6(1H)-one 8.0 g of 5,7-dihydro-2-mercapto-5,5,7,7-tetramethylindeno(5,6-d)imidazol-6(1H)-one were suspended in 100 ml of alcohol in a 250 ml sulfonation flask equipped with stirrer, thermometer, dropping funnel and reflux condenser and treated dropwise while stirring well with a solution of 2.5 g of sodium hydroxide in 50 ml of water. The mixture was stirred at room temperature for an additional 30 minutes, then 5.1 g of 2-chloro-methyl-pyridine hydrochloride were added thereto, the mixture was left to boil at reflux overnight and subsequently evaporated. The residue was taken up in 500 ml of ethyl acetate, extracted with 100 ml of 3N sodium hydroxide, washed neutral with water, dried over sodium sulfate and evaporated in vacuo. The residue, recrystallized from acetonitrile, gave 7.7 g (71.3% of theory) of 5,7-dihydro-5,5,7,7-tetramethyl-2-[(2-pyridylmethyl)thio]indeno(5,6-d)imidazol-6(1H)-one of melting point 167°–168° C.

5,7-Dihydro-5,5,7,7-tetramethyl-2-[[(5-methyl-2-pyridyl)methyl]thio]indeno(5,6-d)imidazol-6(1H)-one of melting point 220°–222° C. was prepared analogously.

Preparation of the starting material 27.8 g of indan-2-one were dissolved in 450 ml of absolute tert.-butanol while gassing with argo and stirring intensively in a 5 l sulfonation flask equipped with stirrer, thermometer, dropping funnel, reflux condenser and calcium chloride tube and then treated with a solution of 141.4 g of potassium tert.-butylate in 859 ml of tert.-butanol. Thereafter there were added directly thereto 358.6 g of methyl iodide in 165 ml of tert.-butanol. The vigorous reaction was cooled occasionally with an ice-bath, temperature rise to 65° C. The mixture was then left to boil under reflux for 2.5 hours bath temperature 70° C. After the first 15 minutes, an additional 94.9 g, of methyl iodide were added dropwise. The cooled suspension was poured into 1.4 l of water and the mixture was extracted with 100 ml of chloroform and then with 500 ml of chloroform. The organic phase was washed with 185 ml of 5% hydrochloric acid and then with 185 ml of water, dried over sodium sulfate and evaporated. Crude yield: 35.6 g (90.5% of theory) of 1,1,3,3-tetramethyl-2-indanone of melting point 65°–75° C. Sample sublimed for microanalysis: melting point 80°–81° C.

18.8 g of 1,1,3,3-tetramethyl-2-indanone were dissolved in 75 ml of sulfuric acid in a 500 ml sulfonation flask equipped with stirrer, thermometer, dropping funnel and calcium chloride tube and nitrated slowly with 75 ml of fuming nitric acid (d=1,5) with intensive stirring and cooling with a $CO_2$/acetone mixture at 0°–5° C. After stirring at room temperature for 2 hours, the mixture was poured into ice/water and extracted with 1 l of ethyl acetate. Then, it was washed with 250 ml of water, 250 ml of 3N soda and 250 ml of saturated sodium chloride solution, dried over sodium sulfate and evaporated. 24.3 g of crystalline crude product were introduced onto a 500 g silicon dioxide column, prepared in toluene, and the column was eluted with toluene/ethyl acetate (1:1). 14.0 g of product of melting point 212°–218° C. were recrystallized from toluene. There were obtained 13.4 g (48.1% of theory) of 1,1,3,3-tetramethyl-5,6-dinitro-2-indanone of melting point 217°–221° C.

12.7 g of 1,1,3,3-tetramethyl-5,6-dinitro-2-indanone were dissolved in 500 ml of methanol in a hydrogenation flask and hydrogenated with Raney-nickel. After the $H_2$-uptake of 6.2 l (theory=6.15 l), the catalyst was removed by filtration under suction, the filtrate was again filtered and then evaporated in vacuo. The residue was crystallized from acetonitrile. There were obtained 9.5 g (95.5% of theory) of 5,6-diamino-1,1,3,3-tetramethyl-2-indanone of melting point 179°–180° C.

20 ml of water and 17.0 g of purified potassium ethylxanthate were added to 20.0 g of 5,6-diamino-1,1,3,3-tetramethyl-2-indanone, dissolved in 200 ml of alcohol, in a 750 ml sulfonation flask equipped with stirrer, thermometer, reflux condenser. The mixture was left to boil at reflux overnight, then diluted with 200 ml of water, neutralized with 20 ml of glacial acetic acid and stirrer at 60°–70° C. for an additional 1 hour. After cooling to 20° C., were removed by filtration under suction. There were obtained 18.8 g (78.9% of theory) of 5,7-dihydro-2-mercapto-5,5,7,7-tetramethylindeno(5,6-d)-imidazol-6(1H)-one with a melting point above 300° C.

EXAMPLE 4

Preparation of 5,7-dihydro-5,5,7,7-tetramethyl-2-[(2-pyridylmethyl)-sulfinyl]inden(5,6-d)imidazol-6(1H)-one 31 ml of a 10% solution of m-chloroperbenzoic acid in ethyl acetate were added dropwise with intensive stirring at 0°–5° C. to 6.16 g of 5,7-dihydro-5,5,7,7-tetramethyl-2-[(2-pyridylmethyl)thio]indeno(5,6-d)-imidazol-6(1H)-one, dissolved in 100 ml of methylene chloride, in a 250 ml sulfonation flask equipped with stirrer, thermometer, dropping funnel and calcium chloride tube. After stirring at 0°–5° C. for 3 hours, the mixture was poured into 1 l of methylene chloride, it was washed twice with 250 ml of 2N soda, then neutral with water, dried over sodium sulfate and evaporated in vacuo. Crystallization of the residue from acetonitrile gave 2.7 g (42.3% of theory) of 5,7-dihydro-5,5,7,7-tetramethyl-2-[(2-pyridylmethyl)sulfinyl]indeno(5,6-d)imidazol-6(1H)-one of melting point 201°–203° C.

EXAMPLE 5

Preparation of 6-[(2-pyridylmethyl)thio]-5H-1,3-dioxolo(4,5-f)-benzimidazole.2HCl 9.8 g of 5H-1,3-dioxolo(4,5-f)-benzimidazole-6-thiol were suspended in 200 ml of alcohol in a 500 ml sulfonation flask equipped with stirrer, thermometer, dropping funnel and reflux condenser and treated dropwise while stirring well with a solution of 4.47 g of sodium hydroxide in 100 ml of water. The mixture was stirred at room temperature for an additional 30 minutes. Then 9.15 g of 2-chloromethyl-5-methylpyridine hydrochloride were added thereto. The mixture was left to boil at reflux overnight and subsequently evaporated. The residue was taken up in 500 ml of ethyl acetate, extracted with 100 ml of 3N sodium hydroxide and washed neutral with water. The aqueous extracts were extracted once more with 500 ml of ethyl acetate. The combined organic phases were dried over sodium sulfate and evaporated in vacuo. After recrystallization from acetonitrile, the residue gave 13.3 g (87.6% of theory) of 6-[[(5-methyl-2-pyridyl)methyl]thio]-5H-1,3-dioxolo(4,5-f)benzimidazole of melting point 187°–188° C. When the residue was dissolved with heating in 50 ml of methanol and treated with 100 ml of 5N hydrochloric acid in ethyl acetate, there were obtained, with the same yield, 16.5 g of dihydrochloride of melting point 232°–234° C.

6-[(2-Pyridylmethyl)thio]-5H-1,3-dioxolo(4,5-f)-benzimidazole.2HCl of melting point 225°–226° C. was prepared according to an analogous process in a yield of 90.3%.

Preparation of the starting material 12.2 g of 1,3-benzodioxole were placed in 75 ml of glacial acetic acid in a 250 ml sulfonation flask equipped with stirrer, thermometer and dropping funnel and then nitrated at 15°–25° C. by the dropwise addition of 9 ml of nitric acid(d=1.4) in 30 ml of glacial acetic acid. The mixture was stirred at room temperature overnight, the precipitated crystals were removed by filtration under suction, washed with water and recrystallized from alcohol. There were obtained 14.0 g of 5-nitro-1,3-benzodioxole of melting point 149°–150° C. and from the mother liquor an additional 2.0 g of melting point 148°–149° C. Total yield: 90.6% of theory.

58.3 g of 5-nitro-1,3-benzodioxole in 3 l of methanol were hydrogenated with Raney-nickel in a 5 l hydrogenation flask. After the uptake of 24.2 l of hydrogen (theory=23.4 l), the catalyst was separated and the solution was evaporated in vacuo. 46.6 g of residue were dissolved in 750 ml of toluene and the solution was left to heat for 2 hours on a steam-bath with 36 ml of acetic anhydride. After evaporation in vacuo, decomposition of the excess of acetic anhydride with methanol and renewed evaporation, 68.8 g of crude product were recrystallized from toluene. There were obtained 56.5 g (90.4%) of 5-acetamino-1,3-benzodioxole of melting point 138°–139° C.

56.5 g of 5-acetamino-1,3-benzodioxole in 250 ml of glacial acetic acid were nitrated as described above with a solution of 30 ml of nitric acid in 100 ml of glacial acetic acid in a 500 ml sulfonation flask equipped with stirrer, thermometer and dropping funnel. The crystals, removed by filtration under suction, were ashed thoroughly with water and dried overnight at about 60° C. in vacuo. There were obtained 68.3 g (96.6% of theory) of 5-acetamino-6-nitro-1,3-benzodioxole of melting point 211°–213° C.

40 g of 5-acetamino-6-nitro-1,3-benzodioxole were dissolved with heating in 4 l of methanol in a 10 l round flask equipped with a reflux condenser. To this hot solution was added a boiling solution of 40 g of sodium methoxide in 4 l of methanol and the mixture was boiled under reflux for exactly 15 minutes. Then, the reaction was interrupted by adding 220 ml of glacial acetic acid. The methanol was removed by distillation and the last traces thereof, together with the glacial acetic acid, were removed by a two-fold evaporation with toluene. The product went into solution with 3 l of methylene chloride and could be freed from the organic residues by suction filtration. The methylene chloride solution was filtered through silicon dioxide and evaporated in vacuo. The residue, recrystallized from isopropanol, gave 30.9 g (95% of theory) of 5-amino-6-nitro-1,3-benzodioxole of melting point 203°–204° C.

18.2 g of 5-amino-6-nitro-1,3-benzodioxole were dissolved in 2 l of methanol in a 4 l hydrogenation flask and hydrogenated with Raney-nickel. After the H$_2$-uptake of 7.0 l, the suspension was filtered under suction into 200 ml of 5N hydrochloric acid in ethyl acetate contained in the suction flask. The catalyst was backwashed well with methanol and the solution was evaporated to a half. The crystals were precipitated with ether. There were obtained 21.0 g (93.4% of theory) of 1,3-benzodioxole-5,6-diamine dihydrochloride, melting point 256°–258° C. (decomposition).

21.0 g of 1,3-benzodioxole-5,6-diamine dihydrochloride were suspended in 300 ml of isopropanol in a 750 ml sulfonation flask equipped with stirrer, thermometer, dropping funnel and reflux condenser. While stirring well there was added dropwise thereto a solution of 10.8 g of potassium hydroxide in 100 ml of water. After adding 17.1 g of purified potassium ethylxanthate, the mixture was left to boil at reflux overnight. Then it was cooled, diluted with 300 ml of water and filtered under suction (fraction 1:5.6 g, melting point above 300° C.). The filtrate was made neutral with glacial acetic acid at 60°–70° C. and stirred at this temperature for 1 hour, then suction-filtered after cooling. This gave an additional 12.1 g of product with a melting point above 300° C. Total yield: 17.7 g (96.2% of theory) of 5H-1,3-dioxolo-(4,5-f)benzimidazole-6-thiol.

EXAMPLE 6

Preparation of 6-[[(5-methyl-2-pyridyl)methyl]sulfinyl]-5H-1,3-dioxolo(4,5-f)benzimidazole 7.7 g of potassium carbonate were added to 11.5 g of 6-[[5-methyl-2-pyridyl)methyl]thio]-5H-1,3-dioxolo(4,5-f)benzimidazole in 1000 ml of methylene chloride in a 2.5 l sulfonation flask equipped with stirrer, thermometer, dropping funnel and calcium chloride tube and a solution of 10 g of n-chloroperbenzoic acid in 100 ml of methylene chloride was added dropwise with intensive stirring at 0°–5° C. After stirring at this temperature for 3 hours, the mixture was poured into 500 ml of ice/water and extracted five times with 500 ml of methylene chloride. The combined methylene chloride extracts were washed with 250 ml of 2N soda and three times with 250 ml of water, dried over sodium sulfate and evaporated in vacuo. The residue, recrystallized from acetonitrile, gave 9.5 g (78.5% of theory) of 6-[[(5-methyl-2-pyridyl)methyl]sulfinyl]-5H-1,3-dioxolo(4,5-f)-benzimidazole of melting point 185°–187° C.

EXAMPLE 7

Preparation of 2-methyl-6-[(5-methyl-2-pyridyl)methyl]-thio-5H-1,3-dioxolo(4,5-f)benzimidazole To 3.9 g of 2-methyl-5H-1,3-dioxolo-(4,5-f)benzimidazole-6-thiol, suspended in 60 ml of alcohol, were added dropwise while stirring 1.57 g of sodium hydroxide in 30 ml of water and, after 30 minutes, there were added 3.44 g of 5-methyl-2-chloromethylpyridine hydrochloride. The mixture was left to boil at reflux overnight, then evaporated and the residue was taken up in 500 ml of ethyl acetate. This was washed with 100 ml of sodium hydroxide three times with 100 ml of water, dried over sodium sulfate and evaporated in vacuo. The crude product was recrystallized from ethyl acetate/petroleum ether (low boiling) and there were obtained 4.8 g (81.7% of theory) of 2-methyl-6-[(5-methyl-2-pyridyl)methyl]-thio-5H-1,3-dioxolo(4,5-f)benzimidazole of melting point 147°–148° C.

2-Methyl-6-[(2-pyridylmethyl)thio]-5H-1,3-dioxolo-(4,5-f)benzimidazole of melting point 155°–156° C. was prepared analogously.

Preparation of the starting material 27.2 g of 2-methyl-1,3-benzodioxole, dissolved in 150 ml of glacial acetic acid, were nitrated at 15°–25° C. with 18 ml of nitric acid (d=1.4) in 50 ml of glacial acetic acid. The precipitated crystals were removed by filtration under suction and recrystallized from methanol. There were obtained 28.8 g (79.6% of theory) of 2-methyl-5-nitrol-1,3-benzodioxole of melting point 84°–95° C. after sublimation at 0.1 mm/70° C.

61.4 g of 2-methyl-5-nitro-1,3-benzodioxole were hydrogenated in 2.5 l of methanol with palladium/carbon 5%. After separating the catalyst, the solution was evaporated and the residue was treated with 40 ml of acetic anhydride in 500 ml of toluene and held at 80° C. for 2 hours. The evaporated crude product was recrystallized from toluene. There were obtained 52.4 g (80.% of theory) of 2-methyl-5-acetamino-1,3-benzodioxole of melting point 155°–156° C.

59.3 g of 2-methyl-5-acetamino-1,3-benzodioxole were nitrated at 15°–25° C. in 225 ml of glacial acetic acid by the dropwise addition of 27 ml of nitric acid in 95 ml of glacial acetic acid. After 30 minutes, the temperature rose spontaneously to 45° C. and the color of the mixture changed from yellow to red. The precipitated crystals were removed by filtration under suction and washed with methanol. There were obtained 64.4 g (88.5% of theory) of 2-methyl-5-acetamino-6-nitro-1,3-benzodioxole of melting point 112°–113° C.

39.6 g of 2-methyl-5-acetamino-6-nitro-1,3-benzodioxole were boiled at reflux for 1 hour in 4 l of methanol with 4 g of sodium methoxide. After adding 5 ml of glacial acetic acid, the solution was evaporated in vacuo. The last traces of glacial acetic acid were removed by evaporation with toluene. The residue was dissolved in methylene chloride and filtered through a small amount of silicon dioxide. The evaporated filtrate was crystallized from isopropanol. There were obtained 29.3 g (90.1% of theory) of 2-methyl-5-amino-6-nitro-1,3-benzodioxole of melting point 139° C.

9.1 g of 2-methyl-5-amino-6-nitro-1,3-benzodioxole were hydrogenated in 1 l of methanol with palladium/-carbon. After the H$_2$-uptake of 3.2 l, the catalyst was separated and 50 ml of 5N hydrochloric acid in ethyl acetate were added to the solution which was then evaporated. The residue was dissolved while heating in alcohol and precipitated with ether. There were obtained 9.9 g (89.1% of theory) of 2-methyl-1,3-benzodioxole-5,6-diamine dihydrochloride of melting point 228°–230° C.

9.9 g of 2-methyl-1,3-benzodioxole-5,6-diamine dihydrochloride were suspended in 125 ml of isopropanol. While stirring there was added dropwise thereto a solution of 4.75 g of potassium hydroxide in 40 ml of water and the mixture was stirred at room temperature for an additional 30 minutes. After adding 7.5 g of purified potassium ethylxanthate, the solution was boiled at reflux overnight, then diluted with 125 ml of water and made neutral with a small amount of glacial acetic acid. The cooled suspension was filtered under suction and the crystals were washed well with water. There were obtained 7.5 g (87.4% of theory) of 2-methyl-5H-1,3-dioxolo(4,5-f)benzimidazole-6-thiol with a melting point above 300° C.

EXAMPLE 8

Preparation of
2,2-dimethyl-6-[(2-pyridyl-methyl)thio]-5H-1,3-dioxolo(4,5-f)benzimidazole To 4.45 g of 2,2-dimethyl-5H-1,3-dioxolo-(4,5-f)benzimidazole-6-thiol, suspended in 100 ml of alcohol, were added dropwise while stirring 1.63 g of sodium hydroxide in 50 ml of water and, after 30 minutes, there were added 3.4 g of 2-chloromethyl-pyridine hydrochloride. The mixture was left to boil at reflux overnight, then evaporated and the residue was taken up in 500 ml of ethyl acetate. This was washed with 100 ml of 3N sodium hydroxide, three times with 100 ml of water, dried over sodium sulfate and evaporated in vacuo. The crude product was recrystallized from acetonitrile. There were obtained 4.6 g (73.4% of theory) of 2,2-dimethyl-6-[(2-pyridyl-methyl)thio]-5H-1,3-dioxolo(4,5-f)benzimidazole of melting point 210°–211° C.

2.1 g of the above substance were dissolved in 30 ml of methanol and treated with 25 ml of 5N hydrochloric acid in ethyl acetate. After evaporation, crystallization from methanol/ether gave 2.2 g of dihydrochloride of melting point 251°–253° C.

2,2-Dimethyl-6-[[(5-methyl-2-pyridyl)methyl]thio]-5H-1,3-dioxolo(4,5-f)benzimidazole of melting point 188°–189° C. and the dihydrochloride of melting point 241°–242° C. was prepared analogously.

Preparation of the starting material

Hydrogen chloride gas was introduced into a solution of 110.1 g of pyrocatechol in 370 ml of acetone for 2 hours while stirring and cooling with ice 10°–15° C. internal temperature, and then for an additional 30 minutes at 0° C. The mixture was poured into ice/water, made alkaline and extracted three times with 1 l of ether. The organic phase was washed neutral three times with 500 ml of water, dried over sodium sulfate and evaporated in vacuo. The residue was distilled in vacuo (b.p. 11 mm/59°–60° C.). There were obtained 39.0 g (26.0% of theory) of 2,2-dimethyl-1,3-benzodioxole.

24 ml of nitric acid (d=1.4) in 60 ml of glacial acetic acid were added dropwise at 15°–20° C. to 39.0 g of 2,2-dimethyl-1,3-benzodioxole in 200 ml of glacial acetic acid. After stirring at room temperature for 3 hours, the mixture was poured into ice/water and extracted twice with 1 l of methylene chloride. The organic phase was washed neutral with water, dried over sodium sulfate and evaporated in vacuo. The residue, recrystallized from methanol, gave 17.0 g (33.5% of theory) of 2,2-dimethyl-5-nitro-1,3-benzodioxole of melting point 88°–90° C.

24.0 g of 2,2-dimethyl-5-nitro-1,3-benzodioxole were hydrogenated in 1.2 l of methanol with palladium carbon (5%). After the H$_2$-uptake of 9.0 l, the catalyst was removed by filtration under suction, the mixture was again filtered and then evaporated. The residue was evaporated twice more with toluene, then dissolved while heating in 200 ml of toluene, treated with 15 ml of acetic anhydride and heated on a steam-bath for 2 hours. The crude produce (27.3 g) obtained after evaporation was dissolved in toluene, placed on 300 g of silicon dioxide and eluted with toluene/ethyl acetate (9:1). After crystallization from ethyl acetate/petroleum ether (low boiling), there were obtained 18.4 g (72.2% of theory) of 2,2-dimethyl-5-acetamino-1,3-benzodioxole of melting point 103°–105° C.

18.4 g of 2,2-dimethyl-5-acetamino-1,3-benzodioxole were nitrated at 15°–25° C. in 90 ml of glacial acetic acid by the dropwise addition of 9.5 ml of nitric acid (d=1.4) in 30 ml of glacial acetic acid. After stirring at room temperature for 3 hours, the suspension was poured into ice/water and the crystals were removed by filtration under suction. These were made into a paste with methanol and again suction filtered. There were obtained 22.0 g (98.2% of theory) of 2,2-dimethyl-5-acetamino-6-nitro-1,3-benzodioxole of melting point 173°–174° C.

22.0 g of 2,2-dimethyl-5-acetamino-6-nitro-1,3-benzodioxole were boiled under reflux for 1 hour in 1.1 of methanol containing 2.2 g of sodium methoxide (10% by weight). After evaporating the solution, the residue was dissolved in methylene chloride, filtered first through Decalit and then through silicon dioxide evaporated and crystallized from isopropanol. There were obtained 17.0 g (92.8% of theory) of 2,2-dimethyl-5-amino-6-nitro-1,3-benzodioxole of melting point 128°–129° C.

17.0 g of 2,2-dimethyl-5-amino-6-nitro-1,3-benzodioxole were hydrogenated in 1 l of methanol with palladium/carbon (5%). After the H$_2$-uptake of 6.0 l, the catalyst was removed by filtration under suction, the solution was filtered and 200 ml of 5N hydrochloric acid in ethyl acetate were added to the filtrate. From the mixture, evaporated to a half, the product crystallized out upon adding 500 ml of ether. There were obtained 18.8 g (91.7% of theory) of 2,2-dimethyl-1,3-benzodioxole- 5,6-diamine dihydrochloride of melting point 233°-235° C.

To 18.8 g of 2,2-dimethyl-1,3-benzodioxole-5,6-diamine dihydrochloride in 250 ml of isopropanol were added first a solution of 8.6 g of potassium hydroxide in 25 ml of water and then 13.7 g of potassium ethylxanthate, and the mixture was left to boil at reflux overnight. The mixture was diluted with 250 ml of water, neutralized with glacial acetic acid and suction filtered. There were obtained 12.9 g (78.2% of theory) of 2,2-dimethyl-5H-1,3-dioxolo(4,5-f)benzimidazole-6-thiol with a melting point above 300° C.

EXAMPLE 9

Preparation of 1,5,6,7-tetrahydro-2-[(2-pyridylmethyl)thio]pyrrolo(2,3-f)benzimidazole trihydrochloride To 2.5 g of 1,5,6,7-tetrahydropyrrolo-(2,3-f)benzimidazole-2-thiol, suspended in 40 ml of alcohol, were added dropwise while stirring 1.2 g of sodium hydroxide in 20 ml of water and, after 30 minutes, there were added 2.4 g of 2-chloromethyl-pyridine hyrochloride. The mixture was left to boil at reflux overnight, then evaporated and the residue was taken up in methylene chloride. The solution obtained was washed with 100 ml of 3N sodium hydroxide and three times with 100 ml of water, dried over sodium sulfate and evaporated in vacuo. The crude product, dissolved in methanol, was treated with 30 ml of hydrochloric acid in ethyl acetate and the precipitated crystals were removed by filtration under suction. There were obtained 1.6 g (31.3% of theory) of 1,5,6,7-tetrahydro-2-[(2-pyridylmethyl)thio]-pyrrolo(2,3-f)benzimidazole trihydrochloride of melting point 207°-209° C.

1,5,6,7-Tetrahydro-2-[[(5-methyl-2-pyridyl)methyl]thio]pyrrolo(2,3-f)benzimidazole trihydrochloride of melting point 205°-210° C. was prepared analogously.

Preparation of the starting material 24.35 g of 5-nitro-indoline were hydrogenated in 1 l of methanol with Raney-nickel. After the H$_2$-uptake of 10 l, the catalyst was separated and the filtrate was evaporated. The residue was dissolved in 500 ml of toluene and the solution obtained was left to heat on a steam-bath with 30.6 ml of acetic anhydride for 1 hour. The crude product obtained after evaporation was recrystallized from acetonitrile. There were obtained 31.1 g (96.1% of theory) of 1,5-diacetamino-indoline of melting point 217°-218° C.

33 g of 1,5-diacetamino-indoline were dissolved at 70° C. in 120 ml of glacial acetic acid and nitrated dropwise with 15 ml of nitric acid (d=1.4). The reaction became vigorous and methanol/ice cooling was used. The precipitated crystals were removed by filtration under suction, dissolved in methylene chloride and washed neutral. After evaporation and crystallization from isopropanol, there were obtained 25 g (62.8% of theory) of 1,5-diacetamino-6-nitro-indoline of melting point 212°-213° C.

21.4 g of 1,5-diacetamino-6-nitro-indoline were dissolved in 2.5 l of methanol, boiled under reflux overnight with 750 ml of 4N hydrochloric acid in methanol and then evaporated. There were obtained 14.2 g (82.5% of theory) of 5-amino-6-nitro-indoline hydrochloride of melting point 259° C.

18.4 g of 5-amino-6-nitro-indoline were hydrogenated in 900 ml of water and 900 ml of methanol with palladium/carbon (5%). After the H$_2$-uptake of 6.1 l, the catalyst was separated, the filtrate was evaporated and the residue, after adding hydrochloric acid in ethyl acetate, was crystallized from isopropanol/ether. There were obtained 14.6 g (76% of theory) of 5,6-diamino-indoline dihydrochloride of melting point 248°-250° C.

Analogous to the reaction with 1,3-benzodioxole-5,6-diamine dihydrochloride (Example 5), from 14.9 g of 5,6-diamino-indoline dihydrochloride there were obtained 6.0 g (54.0% of theory) of 1,5,6,7-tetrahydropyrrolo-(2,3-f)benzimidazole-2-thiol of melting point above 300° C.

EXAMPLE 10

Preparation of 1,5,6,7-tetrahydro-2-[[(5-methyl-2-pyridyl)methyl]thio]indeno(5,6-d)imidazole To 13.5 g of 1,5,6,7-tetrahydroindeno(5,6-d)imidazole-2-thiol, suspended in 200 ml of alcohol, were added dropwise while stirring 5.9 g of sodium hydroxide in 100 ml of water and, after 30 minutes, 13.0 g of 5-methyl-2-chloromethyl-pyridine hydrochloride were added. The mixture was left to boil at reflux overnight, then evaporated and the residue was taken up in methylene chloride. This was washed neutral and, after drying over sodium sulfate, evaporated in vacuo. The residue, recrystallized from acetonitrile, gave 11.9 g (56.9% of theory) of 1,5,6,7-tetrahydro-2-[[(5-methyl-2-pyridyl)-methyl]thiol]indeno(5,6-d)imidazole of melting point 157°-158° C.

The mother liquor was evaporated, the residue was dissolved while heating in methanol, and the solution was treated with 5N hydrochloric acid in ethyl acetate. There was obtained 1,5,6,7-tetrahydro-2-[[(5-methyl-2-pyridyl)methyl]thio]indeno(5,6-d)imidazole dihydrochloride of melting point 246°-247° C.

1,5,6,7-Tetrahydro-2-[(2-pyridylmethyl)thiol]indeno(5,6-d)imidazole of melting point 135°-136° C. and 1,5,6,7-tetrahydro-2-[(2-pyridylmethyl)thio]indeno(5,6-d)imidazole dihydrochloride of melting point 215°-217° C. were obtained analogously.

Preparation of the starting material

5-Nitro-indane was hydrogenated and subsequently acetylated analogously to 5-nitro-1,3-benzodioxole (Example 5). There was obtained 5-acetamino-indane of melting point 111°-112° C.

5-Acetamino-indane was nitrated in glacial acetic acid analogously to 5-acetamino-1,3-benzodioxide (Example 5). There was obtained 5-acetamino-6-nitro-indane of melting point 112°-113° C.

14.6 g of 5-acetamino-6-nitro-indane were boiled under reflux overnight in 1.5 l of methanol with 300 ml of hydrochloric acid in methanol and then evaporated. 11.8 g of crude product were recrystallized from acetonitrile. There were obtained 10.9 g (92.3% of theory) of 5-amino-6-nitro-indane of melting point 131°-132° C.

By hydrogenating 5-amino-6-nitro-indane in alcohol over Raney-nickel, there was obtained 5,6-indane-diamine of melting point 119°–120° C. The dihydrochloride has a melting point of 287°–288° C.

Analogous to the process with 5,6-diamino-1,1,3,3-tetramethyl-2-indanone (Example 3), from 5,6-indanediamine there was obtained 1,5,6,7-tetrahydroindeno-(5,6-d)imidazole-2-thiol with a melting point above 300° C.

EXAMPLE 11

Preparation of 1,5,6,7-tetrahydro-2-[[(5-methyl-2-pyridyl)methyl]sulfinyl]indeno(5,6-d)imidazole 50 ml of a 10% solution of m-chloroperbenzoic acid in ethyl acetate were added dropwise with intensive stirring and at 0°–5° C. to 6.7 g of 1,5,6,7-tetrahydro-2-[[(5-methyl-2-pyridyl)-methyl]thio]indeno(5,6-d)imidazole, dissolved in 200 ml of methylene chloride. After stirring at 0°–5° C. for 3 hours, the mixture was poured into 1 l of methylene chloride, it was washed twice with 250 g of 2N soda, then neutral with water, dried over sodium sulfate and evaporated in vacuo. 6.5 g of crude product were recrystallized from acetonitrile. There were obtained 4.6 g (65.1% of theory) of 1,5,6,7-tetrahydro-2-[[(5-methyl-2-pyridyl)methyl]sulfinyl]indeno(5,6-d)imidazole of melting point 190°–201° C.

1,5,6,7-Tetrahydro-2-[(2-pyridylmethyl)sulfinyl]indeno(5,6-d)imidazole of melting point 173°–174° C. was prepared analogously.

EXAMPLE 12

Preparation of 6,7-dihydro-2-[(2-pyridylmethyl)thio]-1H-p-dioxino(2,3-f)benzimidazole To 4.6 g of 6,7-dihydro-1H-p-dioxino(2,3-f)benzimidazole-2-thiol, suspended in 50 ml of alcohol, were added dropwise while stirring 1.8 g of sodium hydroxide in 25 ml of water and, after 30 minutes, there were added 3.7 g of 2-chloromethyl-pyridine hydrochloride. The mixture was left to boil at reflux overnight, it was then evaporated, and the residue was taken up in methylene chloride. This mixture was washed first with 3N sodium hydroxide, then neutral with water, dried over sodium sulfate and evaporated in vacuo. The crude product was recrystallized from ethyl acetate/petroleum ether. 3.5 g (53% of theory) of 6,7-dihydro-2-[(2-pyridylmethyl)thio]-1H-p-dioxino(2,3-f)benzimidazole of melting point 155°–156° C. were prepared.

6,7-Dihydro-2-[[(5-methyl-2-pyridyl)methyl]thio]-1H-p-dioxino(2,3-f)benzimidazole of melting point 155°–156° C. was prepared analogously.

Preparation of the starting material 6,7-Dihydro-1H-p-dioxino(2,3-f)benzimidazole-2-thiol with a melting point above 300° C. was prepared from 1,4-benzodioxane-6,7-diamine analogously to the process with 5,6-diamino-1,1,3,3-tetramethyl-2-indanone (Example 3).

EXAMPLE 13

Preparation of 1,8-dihydro-2-[[(5-methyl-2-pyridyl)methyl]thio]-m-dioxino(4,5-f)benzimidazole dihydrochloride To 3.7 g of 1,8-dihydro-m-dioxino(4,5-f)benzimidazole-2-thiol, suspended in 60 ml of alcohol, were added dropwise while stirring 1.5 g of sodium hydroxide in 30 ml of water and, after 30 minutes, there were added 3.4 g of 5-methyl-2-chloromethylpyridine hydrochloride. The mixture was left to boil at reflux overnight, then evaporated and the residue was taken up in methylene chloride. This mixture was washed first with 3N sodium hydroxide, then neutral with water, dried over sodium sulfate and evaporated in vacuo. The crude porduct was dissolved while heating in a small amount of methanol and treated with 25 ml of 5N hydrochloric acid in ethylacetate. There was obtained 1,8-dihydro-2-[[(5-methyl-2-pyridyl)methyl]thio]-m-dioxino(4,5-f)benzimidazole dihydrochloride of melting point 153°–155° C.

1,8-dihydro-2-[(2-pyridylmethyl)thio]-m-dioxino(4,5-f)benzimidazole dihydrochloride of melting point 250°–255° C. was obtained analogously.

Preparation of the starting material 100 g of 6-nitro-1,3-benzodioxane 97% were dissolved in 4 l of methanol and hydrogenated with Raney-nickel. After the H$_2$-uptake of 37 l (36 l=theory), the catalyst was removed by filtration under suction and the solution was evaporated. The residue was dissolved in 1 l of toluene and held at 80° C. for 3 hours with 51 ml of acetic anhydride. After evaporation in vacuo, decomposition of the excess acetic anhydride with methanol and renewed evaporation, the crude product was recrystallized from ethyl acetate/petroleum ether (low boiling). 96.7 g (93.4% of theory) of 6-acetamino-1,3-benzodioxane of melting point 133°–134° C. were obtained.

38.6 g of 6-acetamino-1,3-benzodioxane were dissolved in 150 ml of glacial acetic acid and nitrated at 15°–20° C. with 18 ml of nitric acid (d=1.4) in 60 ml of glacial acetic acid. After stirring at room temperature for 3 hours, the precipitated crystals were removed by filtration under suction, dissolved in methylene chloride, washed with 3N sodium hydroxide and water, dried over sodium sulfate, and the solution was concentrated until crystallization set in. Then, it was treated with the same amount of isopropanol. After standing at 0° C. for 30 minutes, the crystals were removed by filtration under suction. This gave 9.3 g of 6-acetamino-7-nitro-1,3-benzodioxane (A) of melting point 185°–186° C. The mother liquor was evaporated in vacuo. The mother liquor containing glacial acetic acid and nitric acid was made alkaline with concentrated sodium hydroxide while cooling with ice and extracted five times with methylene chloride. The combined organic phases were dried over sodium sulfate and treated similarly as above. There were obtained 14.6 g of a crystal mixture of A and 6-acetamino-5-nitro-1,3-benzodioxane (B). From this mixture there could be obtained an additional 2.4 g and from the mother liquor 1.1 g of almost pure A after dissolution in methylene chloride, concentration, treatment with isopropanol and crystallization in an ultrasound bath. Recrystallization gave 2.4 g of pure A. Total: 11.7 g of A (24.5% of theory). From the mixture A:B (1:4) there were separated by silicon dioxide chromatography with methylene chloride/ether (98:2) 6.6 g of pure 6-acetamino-5-nitro-1,3-benzodioxane (B) of melting point 158°–159° C. All other fractions, as well as the mother liquors, were evaporated in vacuo and used as the mixture for the next step and only then separated. The purity was followed by thin-layer chromtography with toluene/ether (1:1). Total yield A+B: 46.7 g (98.1% of theory), the ratio A:B being (2:3).

The cleavage of the acetyl groups is carried out in the case of 6-acetamido-7-nitro-1,3-benzodioxane (A) as well as of A+B mixtures analogously to 5-amino-6-nitro-1,3-benzodioxole (Example 5). For the 6-acetamido-5-nitro-1,3-benzodioxane (B), there was used the process of 2-methyl-5-amino-6-nitro-1,3-benzodioxole (Example 7). From isopropanol there were recrystallized pure 6-amino-7-nitro-1,3-benzodioxane of melting point 181° C. (C) and 6-amino-5-nitro-1,3-benzodioxane of melting point 148°–150° C. (D). The mixture of C and D obtained from A+B was separated by silicon dioxide chromatography with methylene chloride. Thereby, the less polar D was eluted first. In the case of mixed fractions, where C or D (3:1) dominated, they could be purified by recrystallization from methylene chloride so that the recrystallization from isopropanol yielded pure C or D. The purity was followed by thin-layer chromatography with toluene/ethyl acetate (1:1). The total yields were above 90% of theory.

14.4 g of 6-amino-7-nitro-1,3-benzodioxane were hydrogenated in 1 l of methanol with Raney-nickel. After completion of the H$_2$-uptake, the catalyst was separated, the solvent was removed by evaporation in vacuo, and the residue was crystallized from isopropanol. 10.3 g (84.4% of theory) of 1,3-benzodioxane-6,7-diamine of melting point 156–158%. were obtained.

21.2 g of 1,3-benzodioxane-6,7-diamine was dissolved while heating in 300 ml of alcohol, then diluted with 75 ml of water, treated with 23.6 g of potassium ethylxanthate and boiled under reflux overnight. Subsequently, there were added thereto 300 ml of water and at 60°–70° C. 20 ml of glacial acetic acid. After stirring at this temperature for 1 hour, the suspension was cooled, suction filtered and washed with water. 21.6 g (81.2% of theory) of 1,8-dihydro-m-dioxino(5,4-e)benzimidazole-2-thiol of melting point 288°–289° C. were obtained.

EXAMPLE 14

Preparation of
7,8-dihydro-2-[[(5-methyl-2-pyridyl)methyl]thio]-1H,6H-(1,4)dioxepino(2,3-f)benzimidazole and 7,8-dihydro-2-[(2-pyridylmethyl)thio]-1H,6H-(1,4)dioxepino(2,3-f)benzimidazole Analogously to Example 9, from 4.5 g (20.2 mmol) of 7,8-dihydro-1H,6H-(1,4)dioxepino(2,3-f)benzimidazole-2-thiol, there were obtained 5.5 g of 7,8-dihydro-2-[[(5-methyl-2-pyridyl)methyl]thio]-1H,6H-(1,4)dioxepino(2,3-f)benzimidazole of melting point 159°–160° C. and 7,8-dihydro-2-[(2-pyridylmethyl)thio]-1H,6H-(1,4)dioxepino(2,3-f)benzimidazole of melting point 179°–180° C.

Preparation of the starting material 110 g of pyrocatechol, 276 g of potassium carbonate and 303 g of 1,3-dibromopropane were stirred at 120° C. for 48 hours in 800 ml of absolute dimethylformamide. The cooled suspension was filtered under suction, the residue was back-washed with ether and the filtrate was poured into 4 l of water. This was extracted with ether. The ether extract was washed twice with 3N sodium hydroxide and then neutral with water, dried over sodium sulfate and evaporated in vacuo. The residue (146.6 g) was distilled at 11 mm/118°–120° C. 61.9 g (41.2% of theory) of 3,4-dihydro-2H-1,5-benzodioxepine were obtained.

30.0 g of 3,4-dihydro-2H-1,5-benzodioxepine were nitrated at 15°–20° C. in 160 ml of glacial acetic acid and 4 ml of concentrated sulfuric acid by the dropwise addition of 18 ml of nitric acid (d=1.4) in 50 ml of glacial acetic acid. The mixture was stirred at room temperature overnight and then filtered under suction. The material on the suction filter was recrystallized from methanol. There were obtained 27.6 g and, from the mother liquor, an additional 3,3 g (79.2% of theory) of 7-nitro-3,4-dihydro-2H-1,5-benzodioxepine of melting point 111°–112° C.

15.7 g of 7-nitro-3,4-dihydro-2H-1,5-benzodioxepine were hydrogenated in 1 l of methanol with Raney-nickel. After completion of the H$_2$-uptake, the catalyst was separated, the filtrate was evaporated and the residue was heated on a steam-bath for 3 hours in 200 ml of toluene and 11.5 ml of acetic anhydride. After evaporation in vacuo, the crude product was evaporated twice more with toluene and then recrystallized from toluene. 13.5 g (80.9% of theory) of 7-acetamino-3,4-dihydro-2H-1,5-benzodioxepine of melting point 108°–109° C. were obtained.

13.5 g of 7-acetamino-3,4-dihydro-2H-1,5-benzodioxepine were placed in 50 ml of glacial acetic acid and nitrated at 15°–20° C. with 7 ml of nitric acid in 20 ml of glacial acetic acid by dropwise addition, the crystals passing into solution only after the addition of a quarter of the nitric acid. The product separated out, but was stirred for an additional 3 hours, then removed under suction and washed with water and methanol. 15.6 g (94.9% of theory) of 7-acetamino-8-nitro-3,4-dihydro-2H-1,5-benzodioxepine of melting point 139°–140° C. were obtained.

400 ml of 4N hydrochloric acid in methanol were added dropwise at reflux temperature to 22.4 g of 7-acetamino-8-nitro-3,4-dihydro-2H-1,5-benzodioxepine in 2000 ml of methanol, then the mixture was boiled overnight. After evaporation, the residue was taken up in methylene chloride, washed with 2N soda and twice with water, dried over sodium sulfate and again evaporated. The crude product was recrystallized from alcohol. 17.1 g (92.0% of theory) of 7-amino-8-nitro-3,4-dihydro-1H-1,5-benzodioxepine of melting point 125°–126° C. were obtained.

10.2 g of 7-amino-8-nitro-3,4-dihydro-2H-1,5-benzodioxepine were hydrogenated in 500 ml of methanol with Raney-nickel. After separating the catalyst, the solution was evaporated and the residue was recrystallized from ethyl acetate/petroleum either (low boiling). 7.7 g of 3,4-dihydro-2H-1,5-benzodioxepine-7,8-diamine (88.0% of theory) of melting point 97°–102° C. were obtained.

8.5 g (66.4% of theory) of 7,8-dihydro-1H,6H-(1,4)dioxepino(2,3-f)benzimidazole-2-thiol of melting point 297°–298° C. were prepared from 10.4 g of 3,4-dihydro-2H-1,5-benzodioxepine-7,8-diamine analogously to the process with 5,6-diamino-1,1,3,3-tetramethyl-2-indanone (Example 3).

EXAMPLE A

Tablets of the following composition containing as the active substance a compound of formula I or a pharmaceutically acceptable acid addition salt thereof are prepared:

| | | |
|---|---|---|
| 5,7-dihydro-5,5,7,7-tetramethyl-2-[(2-pyridylmethyl)thio]indeno(5,6-d)-imidazol-6-(1H)—one | 50.00 mg | 100.0 mg |
| Lactose (powdered) | 100.00 mg | 150.0 mg |
| Maize starch (white) | 48.0 mg | 145.0 mg |
| Magnesium stearate | 2.0 mg | 5.0 mg |
| | 200.0 mg | 400.00 mg |

The mixture of finely ground 5,7-dihydro-5,5,7,7-tetramethyl-2-[(2-pyridylmethyl)thio]indeno(5,6-d)imidazol-6-(1H)-one, lactose and a part of the maize starch is kneaded with a paste of water and a second portion of the maize starch, granulated, dried and sieved. The granulate is then mixed first with the remainder of the maize starch and thereupon with the magnesium stearate. The mixture is pressed into tablets weighing 200 mg or 400 mg.

We claim:

1. A tricyclic imidazole of the formula

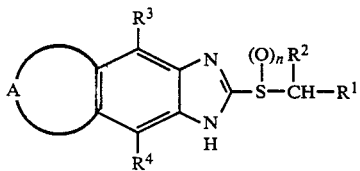

wherein $R^1$ is 2-pyridyl unsubstituted or substituted by lower alkyl or lower alkoxy, n is the integer 0 or 1, $R^2$ is hydrogen or lower alkyl, $R^3$ and $R^4$, independently, are hydrogen or lower alkyl, A is a group of the formula

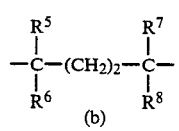

$R^5$, $R^6$, $R^7$ and $R^8$, independently, are lower alkyl or a pharmaceutically acceptable acid addition salt thereof.

2. A compound in accordance with claim 1, wherein $R^2$ is hydrogen.

3. A compound in accordance with claim 1, wherein $R^1$ is 2-pyridyl or 5-methyl-2-pyridyl.

4. 5,6,7,8-tetrahydro-5,5,8,8-tetramethyl-2-[(2-pyridylmethyl)thio]-1H-naphth(2,3-d)imidazole or a pharmaceutically acceptable acid addition salt thereof.

5. 5,6,7,8-tetrahydro-5,5,8,8-tetramethyl-2-[[(5-methyl-2-pyridyl)methyl]thio]-1H-naphth(2,3-d)imidazole or a pharmaceutically acceptable acid addition salt thereof.

6. A pharmaceutical composition containing an amount effective for inhibiting gastric acid secretion of an imidazole of formula

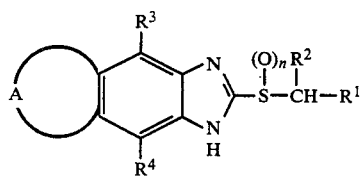

wherein $R^1$ is 2-pyridyl unsubstituted or substituted by lower alkyl or lower alkoxy, n is the integer 0 or 1, $R^2$ is hydrogen or lower alkyl, $R^3$ and $R^4$, independently, are hydrogen or lower alkyl, A is a group of the formula

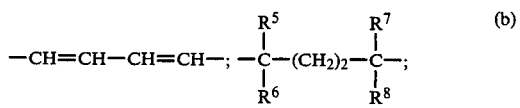

$R^5$, $R^6$, $R^7$ and $R^8$, independently, are lower alkyl and an inert carrier material.

7. A pharmaceutical composition in accordance with claim 6, wherein $R^2$ is hydrogen.

8. A pharmaceutical composition in accordance with claim 7, wherein $R^1$ is 2-pyridyl or 5-methyl-2-pyridyl.

9. A method of inhibiting gastric acid secretion which comprises administering to a warm-blooded animal in need thereof an effective amount of a compound of the formula

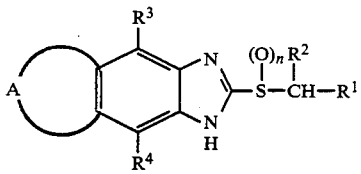

wherein $R^1$ is 2-pyridyl unsubstituted or substituted by lower alkyl or lower alkoxy, n is the integer 0 or 1, $R^2$ is hydrogen or lower alkyl, $R^3$ and $R^4$, independently, are hydrogen or lower alkyl, A is a group of the formula

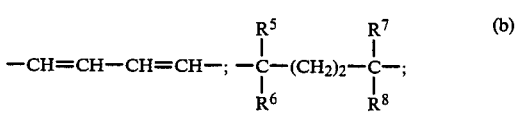

$R^5$, $R^6$, $R^7$ and $R^8$, independently, are lower alkyl.

10. A method of preventing gastric ulcers which comprises administering to a warm-blooded animal in need thereof an effective amount of a compound of formula

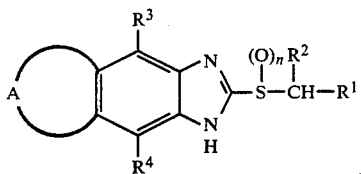

wherein $R^1$ is 2-pyridyl unsubstituted or substituted by lower alkyl or lower alkoxy, n is the integer 0 or 1, $R^2$ is hydrogen or lower alkyl, $R^3$ and $R^4$, independently, are hydrogen or lower alkyl, A is a group of the formula

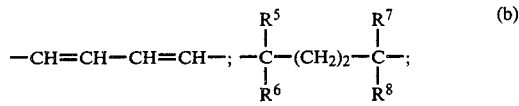

$R^5$, $R^6$, $R^7$ and $R^8$, independently, are lower alkyl.

11. A method in accordance with claim 9, wherein $R^2$ is hydrogen.

12. A method in accordance with claim 11, wherein $R^1$ is 2-pyridyl or 5-methyl-2-pyridyl.

13. A method in accordance with claim 10, wherein $R^2$ is hydrogen.

14. A pharmaceutical composition in accordance with claim 13, wherein the compound of formula I is 5,6,7,8-tetrahydro-5,5,8,8-tetramethyl-2-[(2-pyridylmethyl)thio]-1H-naphth(2,3-d)imidazole, or a pharmaceutically acceptable acid addition salt thereof.

15. A method in accordance with claim 14, wherein the compound of formula I is 5,6,7,8-tetrahydro-5,5,8,8-tetramethyl-2-[(2-pyridylmethyl)thio]-1H-naphth(2,3-d)imidazole, or a pharmaceutically acceptable acid addition salt thereof.

16. A method in accordance with claim 15, wherein the compound of formula I is 5,6,7,8-tetrahydro-5,5,8,8-tetramethyl-2-[(2-pyridylmethyl)thio]-1H-naphth(2,3-d)imidazole, or a pharmaceutically acceptable acid addition salt thereof.

* * * * *

UNITED STATES PATENT AND TRADEMARK OFFICE
CERTIFICATE OF CORRECTION

PATENT NO. : 4,599,347
DATED : July 8, 1986
INVENTOR(S) : Anna Krasso and Henri Ramuz It is certified that error appears in the above-identified patent and that said Letters Patent is hereby corrected as shown below:

In claim 9, column 26, line 65, delete "-CH=CH-CH=CH-".

In claim 10, column 28, line 5, delete "-CH=CH-CH=CH-".

Signed and Sealed this

Second Day of August, 1988

Attest:

DONALD J. QUIGG

*Attesting Officer*   *Commissioner of Patents and Trademarks*